United States Patent [19]

Nakai et al.

[11] Patent Number: 4,510,074
[45] Date of Patent: Apr. 9, 1985

[54] WOOD PRESERVATIVE COMPOSITION

[75] Inventors: Ryozo Nakai; Shigeo Inoue, both of Utsunomiya; Sumio Arai, Yokohama, all of Japan

[73] Assignee: Kao Corporation, Tokyo, Japan

[21] Appl. No.: 482,440

[22] Filed: Apr. 6, 1983

[30] Foreign Application Priority Data

Apr. 30, 1982 [JP] Japan ................... 57-72962

[51] Int. Cl.³ ............... C09K 15/32; C09K 15/22; C09K 15/16; B05D 1/18
[52] U.S. Cl. ............... 252/400R; 106/12; 252/403; 252/405; 427/440
[58] Field of Search ............ 252/403, 405, 400.23; 106/12; 427/440

[56] References Cited

U.S. PATENT DOCUMENTS

| | | | |
|---|---|---|---|
| 3,634,110 | 1/1972 | Varsanyi et al. | 106/12 |
| 4,075,121 | 2/1978 | Konno et al. | 252/403 |
| 4,323,602 | 4/1982 | Parker | 252/403 |
| 4,388,215 | 6/1983 | Ishida et al. | 252/402 |

FOREIGN PATENT DOCUMENTS

| | | | |
|---|---|---|---|
| 0039403 | 3/1983 | Japan | 106/12 |
| 0719869 | 3/1980 | U.S.S.R. | 106/12 |

Primary Examiner—Christine M. Nucker
Attorney, Agent, or Firm—Oblon, Fisher, Spivak, McClelland & Maier

[57] ABSTRACT

Disclosed herein is a wood preservative composition comprising the following ingredients (A) and (B):
(A) at least one alkyl ammonium compound,
(B) at least one polyacid salt selected from the group consisting of condensated homopolyacid salts, condensated heteropolyacid salts, polycarboxylic acid salts and polyphosphonic acid salts.

The (B) ingredients improve the anchoring property of the alkyl ammonium compound (A) which is the active ingredient of a wood preservative, thereby obtained a wood preservative with long-lasting preservation effect under the conditions of underground berrying or underwater installation.

20 Claims, No Drawings

WOOD PRESERVATIVE COMPOSITION

BACKGROUND OF THE INVENTION

1. Field of the Invention

This invention relates to a wood preservative composition and, more specifically, it relates to a wood preservative composition comprising an alkyl ammonium compound as an active ingredient and a polyacid salt having dispersing effect as an auxiliary ingredient.

2. Description of the Prior Art

Wood is one of very important resources as material for telegraph or electric light poles and constructional members such as substrates and posts of houses, as well as for chips as the starting material of paper and pulp. However, since such important wood tends to be rotten by the attack of various types of wood rotting blacket fungi, complete preservation treatment has to be applied so that the wood may not be rotten by the invasion of these fungi. Particularly, since the wood for use in the constructional members are often used during as long as from ten and several years to several decades and wood preservative agents have to possess their effect for a long period in the wood, high stability and low volatility are required for the preservative agents.

For the above requirement, wood preservative agents comprising various types of organic or inorganic compounds as the effective preservative ingredient have hitherto been proposed and used widely.

These wood preservative agents are injected into the wood for applying preservation treatment in various ways such as by pressurized injection, immersion and coating, and the use of a water-soluble wood preservative agent is suited for the pressurized injection. Inorganic preservative agents of copper-chromium-arsenic system (hereinafter simply referred to as CCA) have been used practically at present for the pressurized injection.

However, the CCA preservative agents are much defective in view of the health and sanitation or prevention of circumferential pollutions as below. Specifically, (1) since the CCA system contains those heavy metals extremely toxic to human bodies such as chromium and arsenic, a very strict health-keeping management has to be taken for workers in the step of preservation treatment and a great care has to be paid in the disposal of the treating agent as well, and (2) the CCA system comprises a mixture of heavy metals whose natural resorces have been decreased and restricted.

In view of the above situation, development of less toxic water-soluble preservative agents has been demanded world-wide in place of the toxic CCA preservative agents and general attention has now been directed to alkyl ammonium compounds which are widely utilized in ordinary fungicides as such water-soluble wood preservative agents (hereinafter sometimes referred to as AAC).

The utility of the AAC system as the water-soluble wood preservative agent has gradually been recognized world-wide in recent years in that they have very much excellent performances in the antibacterial effect against the wood rotting bracket fungi, adhesion to the wood, injection into the wood and less toxicity as well. However, the use of the AAC preservative agent to the materials has been hesitated in the case where they are berried in the ground or used under water since it is somewhat inferior to the CCA preservative agent in view of the anchoring property to the wood for a long period.

SUMMARY OF THE INVENTION

In view of such present situation as described above, the present inventors have made an earnest study for the improvement in the anchoring property of AAC absorbed into the wood and, as the result, have accomplished this invention based on the discovery that the anchoring property of AAC absorbed into the wood materials can be improved by blending a polyacid salt having a dispercing effect as an auxiliary ingredient into an aqueous solution of AAC.

Specifically, this invention provides a wood preservative composition comprising the following ingredients (A) and (B):

(A) at least one alkyl ammonium compound, (B) at least one polyacid salt, as aqueous solution thereof, selected from the group consisting of condensated homopolyacid salts, condensated heteropolyacid salts, polycarboxylic acid salts and polyphosphonic acid salts.

DETAILED DESCRIPTION OF THE INVENTION AND PREFERRED EMBODIMENTS

The alkyl ammonium compound as the ingredient (A) in this invention includes, for example, those compounds represented by the general formula (I) or (II):

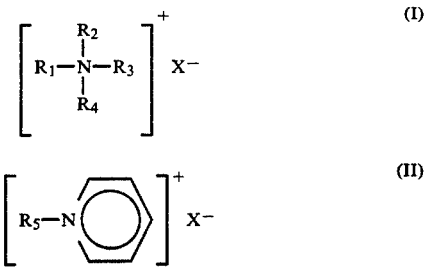

wherein $R_1$ represents an alkyl or alkenyl group of 8–20 carbon atoms, $R_2$ and $R_3$ indivisually represent a hydrogen atom, an alkyl group of 1–5 carbon atoms, a hydroxyalkyl group of 1–5 carbon atoms or an aralkyl group, $R_2$ and $R_3$ being possibly joined to form a ring containing a hetero atom together with an adjacent nitrogen atom, $R_4$ represents a hydrogen atom or an alkyl group of 1–20 carbon aroms, $R_5$ represents an alkyl or alkenyl group of 8–20 carbon atoms and X represents a radical of an organic or inorganic acid.

More preferred compounds of the ingredient (A) include those represented by the formula (I), wherein the cationic moiety comprises lauryldimethylbenzyl ammonium, myristyldimethylbenzyl ammonium, lauryldimethylethylbenzyl ammonium, myristyldimethylethylbenzyl ammonium, lauryltrimethyl ammonium, myristyltrimethyl ammonium, didecyldimethyl ammonium, dicetyldimethyl ammonium, distearyldimethyl ammonium, lauryldimethylhydroxyethyl ammonium, myristyldimethylhydroxyethyl ammonium, cetyldimethylbenzyl ammonium, lauryldimethyl ammonium, myristyldimethyl ammonium, cetyldimethyl ammonium, β-hydroxylauryldimethyl ammonium, β-hydroxymyristyldimethyl ammonium, dodecylmethyl ammonium, lauryldihydroxyethyl ammonium and laurylmorpholinium, as well as those represented by the general formula (II), wherein the cationic moiety comprises laurylpyridinium, cetylpyridinium and the like. As the anionic moiety, halogen atom, radicals of sulfuric acid, acetic acid, glycollic acid, gluconic acid or the like can be mentioned.

Any of the compounds represented by the general formulas (I) and (II) can be synthesized with ease in accordance with known processes.

For the ingredient (B) in this invention, condensated homopolyacid salts include polyphosphate such as pyrophosphate, tripolyphosphate and metaphosphate; polysilicates such as disilicate and tetrasilicate; polyborates such as tetraborate; polymolybdic acids such as tetramolybdic acid and octamolybdic acid; polytungstates such as metatungstate and paratungustate; and polyvanadate such as pyrovanadate and metavanadate. The condensated heteropolyacid salts include phosphomolybdate, borotungstate and silicotungstate.

Further, polyphosphonic acid salts include penta sodium aminotri(methylene phosphonate), polycarboxylic acid salts include citrates, tartarates and polyacrylate. The salt form of these polyacid salts includes sodium salt, potassium salt, ammonium salt and the like. Further, since orthomolybdate, or orthotungstate and orthovanadate, being different from orthophosphate and orthosilicate, easily form polyacid salt in an aqueous solution, they are included within the polyacid salt in this invention.

The property common to each of the members of the ingredient (B) is a dispersing effect. The ingredient (B), together with an alkyl ammonium compound (AAC) as the ingredient (A), forms a salt to cause precipitation at first. Then, as the ingredient (B) is added, the precipitated salt is dispersed again into fine particles almost in a transparent state due to the dispersing effect of the ingredient (B). It is considered that this nature of the ingredient (B) improves the anchoring property of AAC.

The wood preservative composition according to this invention can be obtained by dissolving an ingredient (B) into an aqueous solution of an ingredient (A) in accordance with the conventional process. The concentration for the ingredient (A) in the composition of this invention is between 0.1-20% by weight (hereinafter simply referred to as %) and, preferably, between 0.5-4%. The consentration for the ingredient (B) is between 0.02-10% and, preferably, between 0.1-4%. However, the concentration of these ingredients in the composition may desirably be determined properly depending, e.g., on the type, nature, water content and the processing method of the wood. Further, other preservative agents, insecticides or the like may further be combined with the composition according to this invention.

While any of the known treatments can be used for the wood treating process with composition according to this invention, such as pressurized injection, vacuum treatment, immersion, spraying and coating, the use of pressurized injection is particularly desired.

In wood materials treated by the wood preservative composition according to this invention prepared as above, anchoring property of the composition is improved significantly as compared with those treated only with AAC and the wood preservation effect can last for a long period even under the conditions of underground berrying or under water installation.

Further, since the composition of this invention is less toxic, as well as colorless and odorless, it is very much excellent for the wood preservation.

This invention will now be explained more specifically referring to examples and test examples. However, this invention is no way restricted only to the following Examples.

EXAMPLE 1

The following composition was admixed and agitated in accordance with a conventional method to obtain a wood preservative composition. In the same manner the compositions in Examples 2-8 and the Comparison Example 1 were also obtained.

| (composition) | % |
|---|---|
| Lauryldimethylbenzyl ammonium chloride | 2 |
| Sodium pyrophosphate ($Na_4P_2O_5$) | 2 |
| Water | 96 |
| Total: | 100 |

EXAMPLE 2

| (Composition) | % |
|---|---|
| Lauryldimethylbenzyl ammonium chloride | 2 |
| Sodium tripolyphosphate ($Na_5P_3O_{10}$) | 2 |
| Water | 96 |
| Total: | 100 |

EXAMPLE 3

| (Composition) | % |
|---|---|
| Lauryldimethylbenzyl ammonium chloride | 2 |
| Sodium molybdate ($Na_2MoO_4$) | 2 |
| Water | 96 |
| Total: | 100 |

EXAMPLE 4

| (Composition) | % |
|---|---|
| Myristyldimethylbenzyl ammonium chloride | 2 |
| Sodium tripolyphosphate ($Na_5P_3O_{10}$) | 2 |
| Water | 96 |
| Total: | 100 |

EXAMPLE 5

| (Composition) | % |
|---|---|
| Lauryltrimethylamine acetate | 2 |
| Sodium tripolyphosphate ($Na_5P_3O_{10}$) | 2 |
| Water | 96 |
| Total: | 100 |

EXAMPLE 6

| (Composition) | % |
|---|---|
| Lauryldimethylbenzyl ammonium chloride | 2 |
| Penta sodium aminotri(methylene phosphonate) ($Na_5(N(CH_2PO_3)_3)$) | 2 |
| Water | 96 |

-continued

| (Composition) | % |
|---|---|
| Total: | 100 |

EXAMPLE 7

| (Composition) | % |
|---|---|
| Lauryldimethylbenzyl ammonium chloride | 2 |
| Sodium polyacrylate $\left(\left[\begin{array}{c}-CH_2CH-\\ \vert\\ COONa\end{array}\right]_n\right)$ | 2 |
| Water | 96 |
| Total: | 100 |

EXAMPLE 8

| (Composition) | % |
|---|---|
| Laurylpyridinium chloride | 2 |
| Sodium tripolyphosphate ($Na_5P_3O_{10}$) | 2 |
| Water | 96 |
| Total: | 100 |

COMPARISON EXAMPLE 1

| (Composition) | % |
|---|---|
| Lauryldimethylbenzyl ammonium chloride | 2 |
| Sodium chloride | 2 |
| Water | 96 |
| Total: | 100 |

TEST EXAMPLE 1

The wood preservative compositions of Examples 1–8 were prepared each in 10 g of aqueous solution and absorbed in 5 g of wood flour made from peripheral portion of cedar filled in a glass column (20 mm length × 3 cm inside diameter). Thereafter, in order to evaluate a weather-proof activity, 250 ml of ion-exchanged water is passed to leach out AAC. After leaching, AAC remained in the cedar flour was determined. The results are shown in Table 1.

The AAC remained in the wood flour was determined by the method as below. A chloroform-methylene blue solution was added to the leached aqueous solution and titrated with a standarized solution of sodium laurylsulfate while shaking sufficiently. The point where the blue color of the aqueous layer was completely transferred to the underlying chloroform layer was taken as the end point. The amount of AAC absorbed and remained in the cedar flour was calculated from the titrated value.

TABLE 1

| | Wood preservative composition | Amount of AAC fixed in 1 g cedar flour (mg) |
|---|---|---|
| This invention | Example 1 | 34.3 |
| | Example 2 | 35.9 |
| | Example 3 | 32.5 |
| | Example 4 | 36.0 |
| | Example 5 | 36.2 |
| | Example 6 | 35.0 |

TABLE 1-continued

| | Wood preservative composition | Amount of AAC fixed in 1 g cedar flour (mg) |
|---|---|---|
| | Example 7 | 32.9 |
| | Example 8 | 38.1 |
| Comparative product | Comparison Example 1 | 18.9 |
| | Blended only with 2% AAC | 16.5–18.5 |

It can be seen from above that the products prepared by adding specific polybasic acid salts to AAC have improved anchoring property of AAC as compared with those containing AAC only.

TEST EXAMPLE 2

Wood preservative compositions of Examples 1–8 were prepared each in 50 ml of aqueous solution, to which three wood chips made from peripheral portion of cedar (3 mm × 3 mm × 60 mm) were immersed and left as they were for one hour to absorb the chemicals and they were used as test samples. After air-drying, the test samples were buried in a natural soils taken from the foot of the mountain, stored under the conditions of 30° C. and 98% humidity to perform rotting test. The berried test samples were taken out from the soils after one month, two month and three month respectively, washed with water and then air dried, for which the degree of rottening was evaluated. The evaluation was conducted by measuring the breaking strength of the test samples using a tensile tester (TENSILON UTM-4-100, Toyo Baldwin Company). The standards for the evaluation were as below.

| Breaking Strength | Degree of rottening |
|---|---|
| —: Greater than 0.8 kg | Not rotten at all |
| +: 0.6–0.8 kg | Slightly rotten |
| ++: 0.4–0.6 kg | Moderately rotten |
| +++: Less than 0.4 kg | Severely rotten |

TABLE 2

| | Wood preservating composition | Elapse of time (months) | | |
|---|---|---|---|---|
| | | One month | Two months | Three months |
| This invention | Example 1 | — | — | — |
| | Example 2 | — | — | — |
| | Example 3 | — | — | + |
| | Example 4 | — | — | — |
| | Example 5 | — | — | — |
| | Example 6 | — | — | — |
| | Example 7 | — | — | — |
| | Example 8 | — | — | — |
| Comparative product | Comparison Example 1 | — | + | ++ |
| | Blended only with 2% AAC | — | + | ++ |
| Control | none | ++ | +++ | +++ |

As can be seen from the above, the products incorporated with specific polybasic acid salts to AAC have improved anchoring property of AAC as compared with those containing AAC only in view of aging.

What is claimed is:
1. A wood preservative composition comprising:
(A) an alkyl ammonium compound of the formula (I):

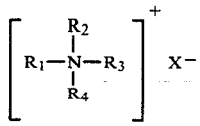

or a mixture thereof; and
(B) a polyacid salt of the formula II;

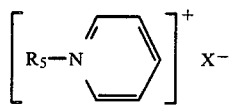

or a mixture thereof; as aqueous solution thereof, wherein:

$R_1$ represents an alkyl or alkenyl group of 8–20 carbon atoms, $R_2$ and $R_3$ individually represent a hydrogen atom, an alkyl group of 1–5 carbon atoms, a hydroxyalkyl group of 1–5 carbon atoms or an aralkyl group, or $R_2$ and $R_3$ may be joined to form a ring containing a hetero-atom together with an adjacent nitrogen atom, $R_4$ represents a hydrogen atom or an alkyl group of 1–20 carbon atoms, $R_5$ represents an alkyl or alkenyl group of 8–20 carbon atoms, and X represents a radical of an organic or inorganic acid.

2. The wood preservative of claim 1 wherein the cationic moiety of (A) is selected from the group consisting of lauryldimethylbenzyl ammonium, myristyldimethylbenzyl ammonium, lauryldimethylethylbenzyl ammonium, myristyldimethylethylbenzyl ammonium, lauryltrimethyl ammonium, myristyltrimethyl ammonium, didecyldimethyl ammonium, dicetyldimethyl ammonium, distearyldimethyl ammonium, lauryldimethylhydroxyethyl ammonium, myristyldimethylhydroxyethyl ammonium, cetyldimethylbenzyl ammonium, lauryldimethyl ammonium, myristyldimethyl ammonium, cetyldimethyl ammonium, β-hydroxylauryldimethyl ammonium, β-hydroxymyristyldimethyl ammonium, dodecylmethyl ammonium, lauryldihydroxyethyl ammonium and laurylmorpholinium.

3. The wood preservative of claim 1 wherein the cationic moiety of (B) is selected from the group consisting of laurylpyridinium and cetylpyridinium.

4. The wood preservative of claim 1 wherein $X^-$ is selected from the group consisting of a halide, and anions of sulfuric acid, acetic acid, glycollic acid, or gluconic acid.

5. The wood preservative of claim 1 wherein $X^-$ is selected from the group consisting of polyphosphates, polysilicates, polyborates, polymolybdic acids, polytungstates and polyvanadate.

6. The wood preservative of claim 5 wherein
the polyphosphate is selected from the group consisting of pyrophosphate, tripolyphosphate and metaphosphate;

the polysilicates are selected from the group consisting of disilicate and tetrasilicate;

the polyborate is tetraborate;

the polymolybdic acid is selected from the group consisting of tetramolybdic acid and octamolybdic acid;

the polytungstate is selected from the group of metatungstate and paratungstate; and the polyvanadate is selected from the group consisting of pyrovanadate and metavanadate.

7. The wood preservative of claim 5 wherein $X^-$ is derived from a heteropolyacid salt selected from the group consisting of phosphomolybdate, boratungstate and silicatungstate.

8. The wood preservative of claim 5 wherein the polyphosphonic acid salt (B) is selected from the group consisting of pentasodium aminotri(methylene phosphonate), citrates, tartarates and polyacrylate.

9. The wood preservative of claim 1 wherein the salt of (B) is formed with a cation selected from the group consisting of sodium, potassium and ammonium.

10. The wood preservative of claim 5 wherein $X^-$ is selected from the group consisting of orthomolybdate, orthotungstate, orthovanadate, orthophosphate and orthosilicate.

11. The wood preservative of claim 1 wherein
(A) is between about 0.1 and 20% by weight of the composition; and
(B) is between about 0.02 and 10% of the composition.

12. The wood preservative of claim 11 wherein:
(A) is between about 0.5 and 4% by weight of the composition; and
(B) is between about 0.1 and 4% of the composition.

13. The wood preservative of claim 1 wherein
(A) is lauryldimethylbenzyl ammonium chloride; and
(B) is sodium pyrophosphate.

14. The wood preservative of claim 13 wherein
(B) is sodium tripolyphosphate.

15. The wood preservative of claim 13 wherein
(B) is sodium molybdate.

16. The wood preservative of claim 1 wherein
(A) is myristyldimethylbenzyl ammonium chloride; and
(B) is sodium tripolyphosphate.

17. The wood preservative of claim 1 wherein
(A) is lauryltrimethylamine acetate; and
(B) is sodium tripolyphosphate.

18. The wood preservative of claim 1 wherein
(A) is lauryldimethylbenzyl ammonium chloride; and
(B) is pentasodiumaminotri(methylenephosphonate).

19. The wood preservative of claim 18 wherein
(B) is sodium polyacrylate

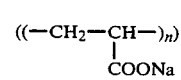

20. The wood preservative of claim 1 wherein
(A) is laurylpyridinium chloride; and
(B) is sodium tripolyphosphate.

* * * * *